United States Patent
Oben

(10) Patent No.: US 9,480,724 B2
(45) Date of Patent: *Nov. 1, 2016

(54) IRVINGIA GABONENSIS TO TREAT AND PREVENT METABOLIC SYNDROME AND REDUCE TOTAL CHOLESTEROL, LDL CHOLESTEROL, BLOOD GLUCOSE, C-REACTIVE PROTEIN, AND LEPTIN LEVELS AND INCREASING ADIPONECTIN LEVELS

(71) Applicant: Julius Enyoug Oben, Cameroon (CM)

(72) Inventor: Julius Enyoug Oben, Cameroon (CM)

( * ) Notice: Subject to any disclaimer, the term of this patent is extended or adjusted under 35 U.S.C. 154(b) by 266 days.

This patent is subject to a terminal disclaimer.

(21) Appl. No.: 14/242,749

(22) Filed: Apr. 1, 2014

(65) Prior Publication Data

US 2014/0212528 A1    Jul. 31, 2014

Related U.S. Application Data

(62) Division of application No. 12/576,113, filed on Oct. 8, 2009, now abandoned.

(60) Provisional application No. 61/106,508, filed on Oct. 17, 2008.

(51) Int. Cl.
*A61K 36/00* (2006.01)
*A61K 36/185* (2006.01)

(52) U.S. Cl.
CPC .................................. *A61K 36/185* (2013.01)

(58) Field of Classification Search
None
See application file for complete search history.

(56) References Cited

PUBLICATIONS

Ngondi et al, The effect of Irvingia gabonensis seeds on body weight and blood lipids of obese subjects in Cameroon. Lipids in Health and Disease (2005), 4.*

* cited by examiner

*Primary Examiner* — Qiuwen Mi
(74) *Attorney, Agent, or Firm* — Steve P. Hassid; Partners Law Group, Inc.

(57) ABSTRACT

In one embodiment, a method is provided for lowering C-reactive protein levels in a mammal. The method comprises administering a composition containing an effective amount of *Irvingia gabonensis* seed to a mammal to reduce C-reactive protein levels in the mammal. Other embodiments include, among other things, lowering leptin levels, increasing adiponectin levels, reducing body weight, decreasing LDL and total cholesterol levels, increasing fat loss, and reducing waist size in a mammal using administering a composition containing an effective amount of *Irvingia gabonensis*.

1 Claim, No Drawings

IRVINGIA GABONENSIS TO TREAT AND PREVENT METABOLIC SYNDROME AND REDUCE TOTAL CHOLESTEROL, LDL CHOLESTEROL, BLOOD GLUCOSE, C-REACTIVE PROTEIN, AND LEPTIN LEVELS AND INCREASING ADIPONECTIN LEVELS

RELATED APPLICATION

This application is a divisional of U.S. application Ser. No. 12/576,113, filed on Oct. 8, 2009 which claims priority to U.S. Provisional Application Ser. No. 61/106,508, filed Oct. 17, 2008, both of which are incorporated herein by reference.

BACKGROUND

Metabolic syndrome, like many other obesity-related conditions, is on the rise in Cameroon and other parts of the world. Experiments were performed to determine, among other things, whether *Irvingia gabonensis*, an extract of the West African plant, could be used as a treatment for metabolic syndrome, to reduce total cholesterol, LDL cholesterol, blood glucose, C-reactive protein, and leptin levels and increase adiponectin levels in a mammal.

Methods: A ten-week, randomized, double-blind, placebo-controlled study was performed involving 102 healthy, overweight and obese participants (53% male, 47% female, ages 19-50; mean age=34). The subjects were randomly divided into two equal groups—placebo and IGOB131 treatment, and all received one 150 mg capsule containing placebo or extract twice a day before meals. A total of nine anthropomorphic and serological measurements were taken at baseline and at four, eight, and ten weeks.

Results: Compared to the placebo group, the IGOB131 group showed a statistically significant different on all nine variables by week ten. These included the three anthropomorphic variables (body weight, body fat, waist size) and the six measures of serological levels (plasma total cholesterol, LDL cholesterol, blood glucose, C-reactive protein, adiponectin, and leptin).

Conclusion: Serum leptin levels were lower in the IGOB131 group while their serum adiponectin level was higher. These results, combined with those on the other seven variables, suggest that the *Irvingia gabonensis* extract, IGOB131, may be used to manage metabolic syndrome through control of obesity and lipid profile.

SUMMARY

Obesity, once considered a major health problem in developed countries, is now on the increase worldwide; e.g., in Cameroon, the reported incidence of obesity in urban areas ranges from 17-21% (Sobngwi et al., 2002; Pasquet et al., 2003). This high incidence reflects the social, nutritional, and lifestyle changes involved in rural-urban migration and the urbanisation of rural areas. As in other countries, urbanisation in Cameroon has also led to an increased incidence of other non-communicable diseases related to obesity (Sobngwi et al., 2002). Obvious causes include the change from a high-fiber to a high-fat diet and a reduction in physical activity (Lee et Sobal, 2003; Cabellero, 2001; Galal, 2002). Obesity, coupled with an unbalanced diet and still largely unknown genetic factors, interact to produce a cluster of metabolic cardiovascular risk factors, including type-2 diabetes mellitus, essential hypertension, dyslipidemia, and ischemic heart disease—known as the metabolic syndrome (Reaven, 1989).

Metabolic syndrome, like many other obesity-related conditions, is on the rise in Cameroon (Mandob et al., 2008) and other parts of the world (Ford and Butt, 2002; Movakovic and Popovic, 2001). The National Cholesterol Education Program Adult Treatment Panel III defined metabolic syndrome traits as the conjoint presence of the following factors: blood pressure elevation, low HDL cholesterol, high triglycerides, and hyperglycemia (NCEP-ATP III, 2002). Adipose tissues are known to store triglycerides and release free fatty acid/glycerol in response to changing energy demands (Spiegelman and Flier, 1996). The adipose tissue also regulates energy homeostasis by secreting biologically active adipocytokines, such as adiponectin, adipsin, leptin, plasminogen activator inhibitor-1, resistin, and tumor necrosis factor (Mohamed-Ali et al., 1998).

Obesity and metabolic syndrome are also associated with inflammation, as seen by an increase in C-reactive protein (CRP) (Marjolein et al., 1999). People with a greater number of metabolic syndrome components generally show higher CRP levels, thus permitting CRP's use as an indicator of metabolic syndrome severity.

Although caloric restriction and weight reduction are beneficial in enhancing insulin action on peripheral tissues (Goodpaster et al., 1999), Kelley et al., 1999) and preventing the development of type 2 diabetes (Knowler et al., 2002), popular weight loss tactics have not taken into consideration the complex nature of this condition. In general (other than recommending healthy lifestyle activities and calorie reduction), popular weight loss products target a single mechanistic path (e.g., fat blocking, appetite suppression, cortisol inhibition, central nervous system stimulation, etc.). In contrast to this type of single-focus approach, preliminary research has already illustrated the healthy effects of *Irvingia gabonensis* extract (IGOB131) in overweight and obese humans on a variety of physiological dimensions, including weight, body composition factors, various blood lipid fractions, antioxidant activity, inflammation, blood glucose, cardiovascular health factors, and gene expression.

IGOB131 extract is obtained from a sweet fleshy fruit (resembling a mango) borne by the West African culinary plant, *Irvingia gabonensis* (*Irvingiaceae*). The plant's leaves and seeds have traditionally been valued for the treatment of dysentery and soup-thickening, respectively. The seeds, moreover, contain naturally high levels of oils, albumin proteins, soluble fibers, and antioxidants. Thus, the purpose of this randomized, double-blind, placebo-controlled clinical study was to assess the possibility of the multi-faceted IGOB131 extract as a tool in the management of metabolic syndrome, among other things.

DETAILED DESCRIPTION

Methods
Participants:
Participants (age 19-50) were recruited from the global population of the city of Yaoundé, Cameroon through radio advertisements and posters. Inclusion criteria included: (1) being a basically healthy person; (2) not having a current/recent cold or flu; (3) having a BMI between 26 kg/m$^2$ and 40 kg/m$^2$; (4) not following any particular dietary regimen; (5) not currently following a weight loss program (6) being a non-smoker; (7) able to cope with multiple blood sampling; and (8) willingness to sign the consent form.

Based on the above criteria, 102 persons were selected to participate in an information session in which the nature, purpose, and potential risks of the study were clearly explained. All participants gave their written informed consent before the study began. The protocol was approved by the Cameroon National Ethics Committee; the study was conducted in accord with the Helsinki Declaration (1983 version).

Study Design/Intervention:

The study was a randomized, double-blind, placebo-controlled design. The 102 West African participants were randomly divided into two groups: placebo (n=50); IGOB131 (n=52). The demographics for the two groups were very similar.

Placebo group: males=27, females=23; mean age=34
IGOB group: males=27, females=25; mean age=34

Five subjects in the placebo group versus six subjects in the treatment group had a family history of diabetes. One subject in the placebo group versus three in the treatment group had a history of gestational diabetes. Body weight, body fat percentage, and waist size were also monitored at the same time. No major dietary changes or physical exercises were suggested during the course of the study.

Test Materials:

All test materials were supplied by Gateway Health Alliances, Inc. (Fairfield, Calif., USA) in individual packets of capsules. The identical-looking placebo and active formulation capsules contained, respectively, a maize-based powder consisting of 150 mg starch, or a maize-based powder containing 150 mg IGOB131.

Sample Collection:

The participants consumed either one capsule of placebo or IGOB131 twice daily before meals. Fasting blood samples (5 ml of blood) were collected at baseline, and at four, eight, and ten weeks after product administration. Blood collection was performed by means of venipuncture coupled to vacutainer tubes. The serum was prepared after blood centrifugation, split into 500 μl aliquots and stored at −20 degrees C. until needed to assess changes in the biochemical parameters; i.e., blood cholesterol, fasting blood glucose, C-reactive protein, adiponectin, and serum leptin.

Anthropometric Measurements

Anthropometric measurements (body weight, percent body fat, and waist circumference were assessed using a Tanita™ BC-418 Segmental Body Composition Analyzer/Scale that uses bio-electrical impedance analysis for body composition analysis. Height was measured with a standard tape measure affixed to a wall while the subject stood on a level, hard surface. Hip and waist measures were obtained with a flexible tape measure, without restrictive garments, to the nearest 0.1 cm. Waist circumference was measured mid-point between the bottom rib and hip bone, taking care to keep the tape in contact with the curve of the back. Hip circumference was obtained at the widest point of the hip. Participants were measured at approximately the same time of day each visit to ensure consistent results.

Analytical Methods:

Serum total cholesterol was assayed using the cholesterol oxidase method, (Richmond, 1973) while triglycerides were determined using the method described by Buccolo and David (1973), serum glucose was measured enzymatically (Trinder, 1969). Quantitative determinations of C-reactive protein (CRP) were determined in duplicate using a high sensitivity immunoassay (Oxis International, Foster City, Calif. USA). Serum leptin was determined in duplicate using an enzyme-linked immunosorbent assay (ELISA) (Diagnostic Systems Laboratory, Webster, Tex. USA). All samples were run in the same assay with an intra-assay variance of 3.2%. Serum adiponectin was determined in duplicate using an enzyme immunoassay (APLCO Diagnostics, Salem, N.H. USA). All samples for each hormone were determined in the same assay to avoid inter-assay variance. Assay intra-assay variance was ≤5%.

Statistical Analysis:

The data for each parameter was summarized (n, mean, and standard deviation) for Week Zero (Initial) and Weeks Four, Eight, and Ten, and for the intra-group percent differences (Initial versus Weeks Four, Eight, and Ten). Several measurements were made for each parameter. The percent change from baseline was tested for differences using the Mixed Effects Mode—a flexible tool for analyzing longitudinal and repeated treatments. Statistical Package for the Social Sciences (SPSS) software was used for all statistical analysis.

Results

Anthropomorphic Characteristics (Body Weight, Body Fat Percentage, Waist Size)

The IGOB131 (versus placebo) group showed a significant decrease in all three variables by week four, with the magnitude of the differences continuing to increase throughout the trial period. By week ten, the differences in measures of body weight, body fat percentage, and waist size between the treatment and placebo groups were all statistically significant at the $p<0.01$ level (Tables 1, 2, 3).

Body Weight (Table 1):

After four weeks of treatment, the placebo group lost 0.6 kg compared to the IGOB131 group, which lost 3.6 kg (3.7%). To translate the difference in amounts lost to final outcomes, the ten-week mean body weight of the placebo group was 95.7 kg versus 85.1 kg for the treatment group ($p<0.01$). In terms of intra-group mean percent change in body weight from baseline to ten weeks, the placebo and treatment groups lost 0.7% and 13.1% ($p<0.01$), respectively.

Body Fat Percentage (Table 2):

As was true of body weight, the placebo group showed no significant change (1.4%) in %-body fat after 4 weeks compared to the IGOB131 group, which lost 2.6%-body fat (a 7.49% reduction). To translate the difference in amount lost to final outcomes, the ten-week mean body fat percentage of the placebo group was 32.7% versus 27.9% for the treatment group ($p<0.05$). In terms of intra-group mean percent change from baseline to ten weeks, the placebo and treatment groups lost 5.7% and 18.4% ($p<0.05$), respectively.

Waist Size (Table 3):

Waist circumference appears to be one of the most important determinants in the diagnosis of metabolic syndrome and obesity. Although the placebo group showed a 3.7 cm decrease after four weeks, the IGOB131 group lost 7.1 cm. By week ten, the 5.3 cm reduction in waist size for the placebo group was less than one-third the 17.0 cm reduction shown by the treatment group ($p<0.01$). In terms of intra-group mean percent change in waist size from baseline to ten weeks, the placebo and treatment groups lost 5.0% and 16.2% ($p<0.01$).

Serological Characteristics—I (Total Cholesterol, LDL Cholesterol, Fasting Blood Glucose)

As shown in Tables 4, 5, and 6, the IGOB131 treatment (versus placebo) group showed a large decrease in these three variables by week four. As with the three anthropomorphic variables (see above), the magnitude of the losses continued to increase throughout the entire ten-week trial period.

Plasma Total Cholesterol Level (Table 4):

In contrast to the small (1.34 mg/dL) decrease shown by the placebo group, by week four the reduction for the IGOB131 group was 18.0 mg/dL (11.9%). To translate the difference in the amounts of decrease to final outcomes, the ten-week mean total cholesterol level of the placebo group was 142.5 mg/dL versus 111.9 mg/dL for the treatment group (p<0.05). In terms of intra-group mean percent change from baseline to ten weeks, the decreases made by the placebo and treatment groups were 1.9% versus 26.2% (p<0.05).

Plasma LDL Cholesterol Level (Table 5):

Again, in contrast to the small (0.96 mg/dL) decrease in LDL shown by the placebo group, by week four the reduction for the IGOB131 group was 10.4 mg/dL (12.6.0%). To translate the difference in the amounts decreased to final outcomes, the ten-week mean LDL cholesterol level of the placebo group was 4.8 mg/dL versus 27.30 mg/dL for the treatment group (p<0.05). In terms of intra-group mean percent change from baseline to ten weeks, the decreases made by the placebo and treatment groups were 4.8% versus 27.30% (p<0.01).

Fasting Blood Glucose Levels (Table 6):

As with the measures of cholesterol levels (above), the small (1.9 mg/dL) decrease in blood glucose level shown by the placebo group by week four can be contrasted with the large 8.91 mg/dL decrease (10.4%) shown by the IGOB131 group. To translate the difference in amounts decreased to final outcomes, the ten-week mean blood glucose level of the placebo group was 77.1 mg/dL versus 66.3 mg/dL for the treatment group (p<0.05). In terms of intra-group mean percent change from baseline to ten weeks, the decreases made by the placebo and treatment groups were 5.3% versus 22.5% (p<0.05).

Serological Characteristics—II (C-Reactive Protein, Adoponectin, Leptin)

As shown in Tables 7, 8, and 9, the IGOB131 treatment (versus placebo) group showed large changes in these three variables by week four. The magnitude of the changes increased through week eight and remained constant through week ten.

C-Reactive Protein Levels (Table 7):

In contrast to the minimal (0.017 mg/dL) decrease shown by the placebo group through the entire trial period, by week four the reduction for the IGOB131 group was 0.58 mg/dL (38.9%). To translate the difference in the amounts of decrease to final outcomes, the ten-week mean C-reactive protein level of the placebo group was 1.445 mg/dL versus 0.715 mg/dL for the treatment group (p<0.01). In terms of intra-group mean percent change from baseline to ten weeks, the decreases made by the placebo and treatment groups were 1.2% versus 52.0% (p<0.01).

Adiponectin Levels (Table 8):

In contrast to the small (1.83 mg/I) increase in adiponectin levels shown by the placebo group, by week four the increase for the IGOB131 group was 12.7 mg/dL (104.3%). To translate the difference in the amounts increased to final outcomes, the ten-week mean adiponectin level of the placebo group was 14.9 mg/dL versus 31.6 mg/dL for the treatment group (p<0.05). In terms of intra-group mean percent change from baseline to ten weeks, the increases made by the placebo and treatment groups were 23.4% versus 159.8% (p<0.05).

Leptin Levels (Table 9):

The small (2.0 ng/ml) decrease in blood leptin levels shown by the placebo group by week four can be contrasted with the large 14.8 ng/mL decrease (45.0%) shown by the IGOB131 group. To translate the difference in amounts decreased to final outcomes, the ten-week mean leptin level of the placebo group was 28.4 ng/mL versus 16.9 mg/dL for the treatment group (p<0.01). In terms of intra-group mean percent change from baseline to ten weeks, the decreases made by the placebo and treatment groups were 9.4% versus 48.7% (p<0.01).

Adverse Events

Adverse events with an incidence >3 included headache (5), lack of sleep (6), and gas (6). Since the incidence of all reported side effects was observed in the placebo group as well as in the treatment group, it is probably safe to conclude that the IGOB131 formulation had few, if any, negative side effects.

Discussion

A variety of naturally occurring plant extracts appear to have beneficial effects on animal and human health. Some compounds have attracted considerable attention due to the cumulative evidence of their physiological qualities serving as anti-obesity and anti-diabetic agents, as well as their relative safety (Bhathena et Velasquez, 2002). In accordance with this trend, the present study showed that one of these compounds, the IGOB131 extract, safely and significantly (versus placebo) reduced body weight and visceral fat mass, as well as plasma total and LDL-cholesterol concentrations. The IGOB131 treatment group also showed an increase in plasma adinopectin level and decreases in leptin and CRP levels compared to the placebo group.

Insulin resistance is the hallmark of the metabolic syndrome and is strongly associated with excess adiposity (Kahn et Flier, 2000; Maison et al., 2001). A variety of adipocyte-derived biologically active molecules termed "adipocytokines" have been identified, including leptin, resistin, TNF-α, and IL-6, that may contribute to obesity-linked metabolic abnormalities (Kern et Ranganathan, 2001; McTernan et al., 2002). Since plasma leptin level is closely correlated with the weight of adipose tissue (Friedman et Halaas, 1998), and reports (Uygun et al. 2000) state that a continuous weight gain may result in increased serum leptin, the decreased plasma leptin level associated with IGOB131 treatment may be attributable to the decrease of adipose tissue induced as a consequence of weight loss.

Adipose tissue plays a prominent role in both insulin resistance and the clinical expression of metabolic syndrome, most likely mediated by the increased release and peripheral tissue action of non-esterified fatty acid and by the dysregulated production of adipocyte-secreted proteins, including leptin, adiponectin, resistin, TNF-α, and IL-6 (Hotamisligil et Spiegelman, 1994, Matsuzawa et al., 1999, McTernan et al., 2002). Adiponectin, which is exclusively expressed in adipose tissue and abundant in human plasma, appears to be decreased in individuals with obesity, type 2 diabetes, and coronary heart disease (Weyer et al., 2002; Kumada et al., 2003). Although its physiological role is still unclear, adiponectin may possess insulin-sensitizing, as well as anti-inflammatory and anti-atherogenic properties (Okamoto et al., 2000; Yamauchi et al., 2001; Okamoto et al., 2002; Matsuzawa et al., 2002).

Adiponectin has recently been shown to increase hepatic insulin sensitivity (Combs et al., 2001), to stimulate fatty acid oxidation in liver and skeletal muscle, and to have protective effects on cardiovascular functions (Hu et al., 1996; Yamauchi et al., 2001). There are several reports suggesting that adiponectin directly modulates glucose tolerance and peripheral tissue insulin sensitivity, possibly through AMP kinase activation (Yamauchi et al., 2002; Tomas et al., 2002). Moreover, different modalities of weight loss—as well as peroxisome proliferator-activated receptor-γ (PARR-γ) agonist therapy—have been shown to increase adiponectin levels longitudinally (Yang et al., 2001; Yu et al., 2002). Another study demonstrated that moderate acute weight loss of 5-7% in obese subjects with metabolic syndrome is associated with dramatic improvement in all aspects of the condition, although the individuals remained markedly obese (Case et al., 2002).

The study, which specifically assessed, among other things, adipocytokine variations in a group of obese subjects with metabolic syndrome after a ten week IGOB131 treatment, showed a marked improvement in glucose associated with a significant change in adiponectin levels. In general, expression of adiponectin in plasma correlates well with expression in adipose tissue.

The study also measured the anti-metabolic syndrome effects of IGOB131 via body weight, abdominal fat mass, plasma lipids, adiponectin, C-reactive proteins, and leptin levels in obese participants. The extract's efficacy may be a result of the synergistic effects of combining dietary fiber, albumin proteins, and antioxidants in sufficient amounts. The involvement of the soluble fiber fraction with an unstirred water layer present along the luminal surface of mucosa intestinal cells increases the thickness of that layer, thereby forming a physical barrier to the cholesterol absorption (Kritchevsky, 1988; Roberfroid, 1993).

The effectiveness of the IGOB131 extract may also be attributed to the albumin fraction. Earlier human studies on the effect of plant protein revealed that the administration of soy protein to female volunteers with normal lipids levels induced a significant reduction in serum levels of blood lipids. A 1981 study (Wolfe et al., 1981) showed a reduction of both total cholesterol and triglycerides levels in a hypercholesterolemic man who was fed a plant protein diet.

Other studies, similar to the plant albumin ones, have shown the metabolic syndrome-preventive activity of antioxidant components (i.e., vitamin C, polyphenols). Antioxidants, especially epigallocatechin gallate, had antiobesity activity and apparently improved metabolic disorders via modulation of adipokines and growth factors (Kao et al., 2000; Ashida et al., 2004), especially suppression of leptin concentrations (Kao et al., 2000; Ashida et al., 2004; Sayama et al., 2000).

In sum, *Irvingia gabonensis* extract (IGOB131) administered twice a day to healthy, overweight, and obese individuals resulted in weight reduction (body weight, body fat, waist size) and an improvement in the symptoms associated with metabolic syndrome. The extract showed efficacy in the control and lowering of serum total cholesterol, LDL-cholesterol, and serum leptin levels, while the serum adiponectin was higher than in the placebo group. These results suggest that IGOB131 may be used to manage metabolic syndrome through control of obesity and lipid profile.

REFERENCES

1. Sobngwi, E., Mbanya, J. C., Unwin N. C., et al. (2002). Physical activity and its relationship with hypertension and diabetes in urban and rural Cameroon. *Int J Obes Relat Metab Disord;* 26(7):1009-1016.
2. Pasquet, P., Temgoua, L S., Melaman, S F., Froment, A., Rikong, A H. (2003). Prevalence of obesity and overweight for urban adults in Cameroon. *Annal of Human Biology.* 30 (5): 551-562.
3. Lee, K., Sobal, J., (2003). Socio-economic, dietary, activity, nutrition and body weight transitions in South Korea. *Public Health Nutr;* 6(7):665-674.
4. Caballero, B. (2001). Introduction. Symposium: Obesity in developing countries: Biological and ecological factors. *J Nutr.* 131(3):866-870.
5. Galal, O M. (2002). The nutrition transition in Egypt: obesity, undernutrition and the food consumption context. *Public Health Nutr.* 5(1A):141-148.
6. Reaven G M. Role of insulin resistance in human disease. *Diabetes.* 1989; 37:1595-1607.
7. Ford E S, Butt G, Dietz W. Prevalence of the metabolic syndrome among U.S. adults: finding from the 3rd National Health Nutrition Examination Survey. *JAMA.* 2002; 287:356-359.
8. Movakovic B, Popovic M. Occurrence of the metabolic syndrome in the population of the town of Novi Sed. *Med Pregl.* 2001; 54; 17-20.
9. Seidell, J. C. Obesity, insulin resistance and diabetes-a worldwide epidemic. *Br. J. Nutr.* 2001, 83, S5-S8.
10. Third report of the National Cholesterol Education Program (NCEP) Expert Panel on Detection, Evaluation, and Treatment of High Blood Cholesterol in Adults (Adult Treatment Panel III) final report. *Circulation* 106:3143-3121, 2002.
11. Damaris M. Enyegue, J L Ngondi, Agbor A. Gabriel, Julius Oben. Prevalence and prediction of metabolic syndrome in Cameroon. Abstract book, 2nd Conference on Stroke, Hypertension, Diabetes and metabolic syndrome. Prague Czech republic, 2008.
12. Shirai K. Obesity as the core of the metabolic syndrome and the management of coronary heart disease. Curr Med Res Opin 2004; 20:295-304.
13. Isomaa B, Almgren P, Tuomi T, Forsén B, Lahti K, Nisssén M, et al. Cardiovascular morbidity and mortality associated with the metabolic syndrome. Diabetes Care 2001; 24:683-9.
14. Richmond W. Preparation and properties of a cholesterol oxidase from *Nocardia* sp. and its application to the enzymatic assay of total cholesterol in serum. Clin. Chem 1973; 19:1350-6.
15. Buccolo G., David H. Quantitative determination of serum triglycerides by the use of enzymes. Clin. Chem 1973; 19:476-82.
16. Trinder P. Determination of glucose in blood using glucose oxidase with an alternative oxygen acceptor. *Ann Clin Biochem* 1969; 6:24.
17. Marlett J A. Sites and mechanisms for the hypocholesterolemic actions of soluble dietary fiber sources. In: Kritchevsky D, Bonfield C, eds. *Dietary Fiber in Health and Disease.* New York: Plenum Press, 1997:109-21.
18. Marlett J A, Hosig K B, Vollendorf N W, Shinnick F L, Haack V S, Story J A. Mechanism of serum cholesterol reduction by oat bran. Hepatologyl 994; 20:1450-57.
19. Sharma, R. D. (1986b). An evaluation of hypocholesterolemic factor of fenugreek (*T. foenum graecum*) in rats. Nutr. Rep. In, 33, 669-677.
20. Sharma, R. D. (1984). Hypocholesterolcmic activity of fcnugreek (*T. foenuin graccurn*). An experimental study in rats. Nut. Rip. Mt., 30, 221-231.
21. Kritchevsky, D. 1988. Dietary fibre. Ann. Rev. Nutr., 8, 301-328.

22. Roberfroid, M. 1993. Dietary fiber, inulin and oligofructose: a review comparing their physiological effects. Crit. Rev. Food Sci. Nutr., 33(2), 103-148.
23. Caspary, W. F., Elsenhans, B., Sufke, U., Plok, M., Blume, R., Lembcke, B., Creutzfeldt, W. 1980. Effect of dietary fiber on absorption and motility. In: Greidanus, T. J. B. van W. (ed). Frontiers of Hormone Research. Washington, D.C.: National Academy Press, 202-217.
24. Jenkins, D. J. A. 1981. Slow release carbohydrate and the treatment of diabetes. Proc. Nutr. Soc., London, 40, 227-235.
25. Halaas, J. L., Boozer, C., Blair, W. J., Fidahusein, N., Denton, D. A. and Friedman, J. M. (1997) Physiological response to long-term peripheral and central leptin infusion in lean and obese mice. Proc. Natl. Acad. Sci. U.S.A. 94: 8878-8883.
26. Combs, T. P., Berg, A. H., Obici, S., Scherer, P. E. and Rossetti, L. (2001) Endogenous glucose production is inhibited by the adipose-derived protein Acrp30. J. Clin. Invest. 108, 1875-1881.
27. Hu, E., Liang, P. and Spiegelman, B. M. (1996) AdipoQ is a novel adipose-specific gene dysregulated in obesity. J. Biol. Chem. 271, 10697-10703.
28. Yamauchi, T., Kamon, J., Waki, H., Terauchi, Y., Kubota, N., Hara, K., Mori, Y., Ide, T., Murakami, K., Tsuboyama-Kasaoka, N. et al. (2001) The fat-derived hormone adiponectin reverses insulin resistance associated with both lipoatrophy and obesity. Nat. Med. 7, 941-946.
29. Weyer, C., Funahashi, T., Tanaka, S., Hotta, K., Matsuzawa, Y., Pratley, R. E. and Tataranni, P. A. (2001) Hypoadiponectinemia in obesity and type 2 diabetes: close association with insulin resistance and hyperinsulinemia. J. Clin. Endocrinol. Metab. 86, 1930-1935.
30. Lavigne C, Marette A, Jacques H. Cod and soy proteins compared with casein improve glucose tolerance and insulin sensitivity in rats. Am J Physiol Endocrinol Metab 2000; 278:E491-500.
31. Akahoshi A, Koba K, Ichinose F, et al. Dietary protein modulates the effect of CLA on lipid metabolism in rats. Lipids 2004; 39:25-30.
32. Nagasawa A, Fukui K, Kojima M, et al. Divergent effects of soy protein diet on the expression of adipocytokines. Biochem Biophys Res Commun 2003; 311:909-14.
33. Ali A A, Velasquez M T, Hansen C T, Mohamed A I, Bhathena S J. Effects of soybean isoflavones, probiotics, and their interactions on lipid metabolism and endocrine system in an animal model of obesity and diabetes. J Nutr Biochem 2004; 15:583-90.
34. Ali A A, Velasquez M T, Hansen C T, Mohamed A I, Bhathena S J. Modulation of carbohydrate metabolism and peptide hormones by soybean isoflavones and probiotics in obesity and diabetes. J Nutr Biochem 2005; 16:693-9.
35. Bu L, Setchell K D, Lephart E D. Influences of dietary soy isoflavones on metabolism but not nociception and stress hormone responses in ovariectomized female rats. Reprod Biol Endocrinol 2005; 3:58.
36. Szkudelski T, Nogowski L, Pruszynska-Oszmalek E, Kaczmarek P, Szkudelska K. Genistein restricts leptin secretion from rat adipocytes. J Steroid Biochem Mol Biol 2005; 96:301-7.
37. Ae Park S, Choi M S, Cho S Y, et al. Genistein and daidzein modulate hepatic glucose and lipid regulating enzyme activities in C57BL/KsJdb/db mice. Life Sci 2006; 79:1207-13.
38. Wu A H, Stanczyk F Z, Martinez C, et al. A controlled 2-mo dietary fat reduction and soy food supplementation study in postmenopausal women. Am J Clin Nutr 2005; 81:1133-41.
39. Goodman-Gruen D, Kritz-Silverstein D. Usual dietary isoflavone intake is associated with cardiovascular disease risk factors in postmenopausal women. J Nutr 2001; 131:1202-6.
40. Kao Y H, Hiipakka R A, Liao S. Modulation of obesity by a green tea catechin. Am J Clin Nutr 2000; 72:1232-4.
41. Sayama K, Lin S, Zheng G, Oguni I. Effects of green tea on growth, food utilization and lipid metabolism in mice. In Vivo 2000; 14:481-4.
42. Westerterp-Plantenga M S, Lejeune M P, Kovacs E M. Body weight loss and weight maintenance in relation to habitual caffeine intake and green tea supplementation. Obes Res 2005; 13:1195-204.
43. Kahn B B, Flier J S 2000 Obesity and insulin resistance. J Clin Invest 106:473-481.
44. Maison P, Byrne C D, Hales C N, Day N E, Wareham N J 2001 Do different dimensions of the metabolic syndrome change together over time? Evidence supporting obesity as the central feature. Diabetes Care 24:1758-1763.
45. Goodpaster B H, Kelley D E, Wing R R, Meier A, Thaete F L 1999 Effects of weight loss on regional fat distribution and insulin sensitivity in obesity. Diabetes 48:839-847.
46. Kelley D E, Goodpaster B, Wing R R, Simoneau J A 1999 Skeletal muscle fatty acid metabolism in association with insulin resistance, obesity, and weight loss. Am J Physiol Endocrinol Metab 277:E1130-E1141.
47. Knowler W C, Barrett-Connor E, Fowler S E, Hamman R F, Lachin J M, Walker E A, Nathan D M 2002 Reduction in the incidence of type 2 diabetes with lifestyle intervention or metformin. N Engl J Med 346:393-403.
48. Matsuzawa Y, Funahashi T, Nakamura T 1999 Molecular mechanism of metabolic syndrome X: contribution of adipocytokines adipocyte-derived bioactive substances. Ann NY Acad Sci 892:146-154.
49. McTernan C L, McTernan P G, Harte A L, Levick P L, Barnett A H, Kumar S 2002 Resistin, central obesity, and type 2 diabetes. Lancet 359:46-47.
50. Hotamisligil G S, Spiegelman B M 1994 Tumor necrosis factor α: a key component of the obesity-diabetes link. Diabetes 43:1271-1278.
51. Weyer C, Funahashi T, Tanaka S, Hotta K, Matsuzawa Y, Pratley R E, Tataranni P A 2001 Hypoadiponectinemia in obesity and type 2 diabetes: close association with insulin resistance and hyperinsulinemia. J Clin Endocrinol Metab 86:1930-1935.
52. Kumada M, Kihara S, Sumitsuji S, Kawamoto T, Matsumoto S, Ouchi N, Arita Y, Okamoto Y, Shimomura I, Hiraoka H, Nakamura T, Funahashi T, Matsuzawa Y 2003 Association of hypoadiponectinemia with coronary artery disease in men. Arterioscler Thromb Vasc Biol 23:85-89.
53. Yamauchi T, Kamon J, Waki H, Terauchi Y, Kubota N, Hara K, Mori Y, Ide T, Murakami K, Tsuboyama-Kasaoka N, Ezaki O, Akanuma Y, Gavrilova O, Vinson C, Reitman M L, Kagechika H, Shudo K, Yoda M, Nakano Y, Tobe K, Nagai R, Kimura S, Tomita M, Froguel P, Kadowaki T 2001 The fat-derived hormone adiponectin reverses insulin resistance associated with both lipoatrophy and obesity. Nat Med 7:941-946.

54. Okamoto Y, Kihara S, Ouchi N, Nishida M, Arita Y, Kumada M, Ohashi K, Sakai N, Shimomura I, Kobayashi H, Terasaka N, Inaba T, Funahashi T, Matsuzawa Y 2002 Adiponectin reduces atherosclerosis in apolipoprotein E-deficient mice. Circulation 106:2767-2770.

55. Okamoto Y, Arita Y, Nishida M, Muraguchi M, Ouchi N, Takahashi M, Igura T, Inui Y, Kihara S, Nakamura T, Yamashita S, Miyagawa J, Funahashi T, Matsuzawa Y 2000 An adipocyte-derived plasma protein, adiponectin, adheres to injured vascular walls. Horm Metab Res 32:47-50.

56. Matsuzawa Y, Funahashi T, Nakamura T 2002 Molecular mechanism of vascular disease in metabolic syndrome X. J Diabetes Complications 16:17-18.

57. Yu J G, Javorschi S, Hevener A L, Kruszynska Y T, Norman R A, Sinha M, Olefsky J M 2002. The effect of thiazolidinediones on plasma adiponectin levels in normal, obese, and type 2 diabetic subjects. Diabetes 51:2968-2974.

58. Yang W S, Lee W J, Funahashi T, Tanaka S, Matsuzawa Y, Chao C L, Chen C L, Tai T Y, Chuang L M 2001 Weight reduction increases plasma levels of an adipose-derived anti-inflammatory protein, adiponectin. J Clin Endocrinol Metab 86:3815-3819.

59. Case C C, Jones P H, Nelson K, O'Brian Smith E, Ballantyne C M 2002 Impact of weight loss on the metabolic syndrome. Diabetes Obes Metab 4:407-414.

60. Bruun J M, Lihn A S, Verdich C, Pedersen S B, Toubro S, Astrup A, Richelsen B 2003 Regulation of adiponectin by adipose tissue-derived cytokines: in vivo and in vitro investigations in humans. Am J Physiol Endocrinol Metab 285:E527-E533.

61. Tomas E, Tsao T S, Saha A K, Murrey H E, Zhang C c C, Itani S I, Lodish H F, Ruderman N B 2002 Enhanced muscle fat oxidation and glucose transport by ACRP30 globular domain: acetyl-CoA carboxylase inhibition and AMP-activated protein kinase activation. Proc Natl Acad Sci USA 99:16309-16313.

62. Yamauchi T, Kamon J, Minokoshi Y, Ito Y, Waki H, Uchida S, Yamashita S, Noda M, Kita S, Ueki K, Eto K, Akanuma Y, Froguel P, Foufelle F, Ferre P, Carling D, Kimura S, Nagai R, Kahn B B, Kadowaki T 2002 Adiponectin stimulates glucose utilization and fatty-acid oxidation by activating AMP-activated protein kinase. Nat Med 8:1288-1295.

63. Ryan A S, Nicklas B J, Berman D M, Elahi D 2003 Adiponectin levels do not change with moderate dietary induced weight loss and exercise in obese postmenopausal women. Int J Obes Relat Metab Disord 27:1066-1071.

64. McTernan C L, McTernan P G, Harte A L, Levick P L, Barnett A H, Kumar S 2002 Resistin, central obesity, and type 2 diabetes. Lancet 359:46-47.

65. Hotamisligil G S, Spiegelman B M 1994 Tumor necrosis factor α: a key component of the obesity-diabetes link. Diabetes 43:1271-1278.

66. Munro J M, Cotran R S. The pathogenesis of atherosclerosis: atherogenesis and inflammation. Lab Invest. 1988; 58:249-261.

67. Alexander R W. Inflammation and coronary artery disease. N Engl J Med. 1994; 331:468-469.

68. de Maat M P, Pietersma A, Kofflard M, Sluiter W, Kluft C. Association of plasma fibrinogen levels with coronary artery disease, smoking and inflammatory markers. Atherosclerosis. 1996; 121:185-191.

69. Berk B C, Weintraub W S, Alexander R W. Elevation of C-reactive protein in 'active' coronary artery disease. Am J Cardiol. 1990; 65:168-172.

70. Thompson S G, Kienast J, Pyke S D M, Haverkate F, van de Loo J C W. Hemostatic factors and the risk of myocardial infarction or sudden death in patients with angina pectoris. European Concerted Action on Thrombosis, and Disabilities Angina Pectoris Study Group. N Engl J Med. 1995; 332:635-641.

71. Biasucci L M, Vitelli A, Liuzzo G, Altamura S, Caligiuri G, Monaco C, Rebuzzi A G, Ciliberto G, Maseri A. Elevated levels of interleukin-6 in unstable angina. Circulation. 1996; 94:874-877.

72. Mendall M A, Patel P, Ballam L, Strachan D, Northfield T C. C-reactive protein and its relation to cardiovascular risk factors: a population based cross sectional study. BMJ. 1996; 312:1061-1065.

73. Ridker P M, Cushman M, Stampfer M J, Tracey R P, Hennekens C H. Inflammation, aspirin and the risk of cardiovascular disease in apparently healthy men. N Engl J Med. 1997; 336:973-979.

74. Koenig W, Froehlich M, Sund M, Doering A, Fischer H G, Loewel H, Hutchinson W L, Pepys M. C-reactive protein (CRP) predicts risk of coronary heart disease (CHD) in healthy middle-aged men: results from the MONICA-Augsburg Cohort Study, 1984/85-1992. Circulation. 1997; 96(suppl 8):I99.

75. Kuller L H, Tracy R P, Shaten J, Meilahn E N, for the MRFIT Research Group. Relation of C-reactive protein and coronary heart disease in the MRFIT nested case-control study. Am J Epidemiol. 1996; 144:537-547.

76. Montague C T, O'Rahilly S: The perils of portliness: causes and consequences of visceral adiposity. Diabetes 49:883-888, 2000.

77. Zhu S, Wang Z, Heshka S, Heo M, Faith M S, Heymsfield S B: Waist circumference and obesity-associated risk factors among whites in the third National Health and Nutrition Examination Survey: clinical action thresholds. Am J Clin Nutr 76:743-749, 2002.

78. Lafontan M: Fat cells: afferent and efferent messages define new approaches to treat obesity. Annu Rev Pharmacol Toxicol 45:119-146, 2004.

79. Xu H, Barnes G T, Yang Q, Tan G, Yang D, Chou C J, Sole J, Nichols A, Ross J S, Tartaglia L A, Chen H: Chronic inflammation in fat plays a crucial role in the development of obesity-related insulin resistance. J Clin Invest 112:1821-1830, 2003.

80. Trujillo M E, Scherer P E: Adiponectin: journey from an adipocyte secretory protein to biomarker of the metabolic syndrome. J Intern Med 257:167-175, 2005.

Tables

TABLE 1

Body weight: effectiveness of IGOB131

| | Body weight (mean kg) | | | | Weight change (%) | | |
|---|---|---|---|---|---|---|---|
| | Initial | 4 weeks | 8 weeks | 10 weeks | 4 Weeks-Initial | 8 Weeks-Initial | 10 Weeks-Initial |
| Placebo | 96.4 ± 12.3 | 95.8 ± 8.2 | 95.1 ± 10.6 | 95.7 ± 15.2 | −0.62 | −1.35 | −0.73 |
| IGOB131 | 97.9 ± 9.1 | 94.3 ± 5.5$^a$ | 89.7 ± 4.7$^a$ | 85.1 ± 3.1$^b$ | −3.68 | −8.38$^†$ | −13.07$^‡$ |

$^a$p < 0.05; $^b$p < 0.01 compared with Placebo
$^†$p < 0.05; $^‡$p < 0.01 compared with Initial; intra-group analysis

TABLE 2

Body fat: effectiveness of IGOB131

| | Body fat (mean %) | | | | Fat reduction (%) | | |
|---|---|---|---|---|---|---|---|
| | Initial | 4 weeks | 8 weeks | 10 weeks | 4 Weeks-Initial | 8 Weeks-Initial | 10 Weeks-Initial |
| Placebo | 34.72 ± 8.60 | 33.31 ± 10.86 | 32.99 ± 11.93 | 32.73 ± 15.71 | −4.06 | −4.98 | −5.73 |
| IGOB131 | 34.17 ± 7.96 | 31.61 ± 5.42$^a$ | 28.19 ± 6.63$^a$ | 27.88 ± 5.51$^a$ | −7.49$^†$ | −17.50$^†$ | −18.41$^†$ |

$^a$p < 0.05; $^b$p < 0.01 compared with Placebo
$^†$p < 0.05; $^‡$p < 0.01 compared with Initial; intra-group analysis

TABLE 3

Waist size: effectiveness of IGOB131

| | Waist (mean cm) | | | | Waist change (%) | | |
|---|---|---|---|---|---|---|---|
| | Initial | 4 weeks | 8 weeks | 10 weeks | 4 Weeks-Initial | 8 Weeks-Initial | 10 Weeks-Initial |
| Placebo | 106.40 ± 10.83 | 102.73 ± 10.63 | 101.10 ± 14.89 | 101.11 ± 15.86 | −3.45 | −4.98 | −4.97 |
| IGOB131 | 105.11 ± 6.38 | 98.01 ± 8.44$^a$ | 90.11 ± 8.70$^a$ | 88.10 ± 7.6$^b$ | −6.75$^†$ | −14.27$^†$ | −16.18$^‡$ |

$^a$p < 0.05; $^b$p < 0.01 compared with Placebo
$^†$p < 0.05; $^‡$p < 0.01 compared with Initial; intra-group analysis

TABLE 4

Plasma total cholesterol level: effectiveness of IGOB131

| | Total cholesterol (mean mg/dL) | | | | Change (%) | | |
|---|---|---|---|---|---|---|---|
| | Initial | 4 weeks | 8 weeks | 10 weeks | 4 Weeks-Initial | 8 Weeks-Initial | 10 Weeks-Initial |
| Placebo | 145.28 ± 22.40 | 143.94 ± 12.21 | 142.11 ± 13.66 | 142.47 ± 12.17 | −0.92 | −2.18 | −1.93 |
| IGOB131 | 151.74 ± 18.52 | 133.74 ± 16.63$^a$ | 120.18 ± 11.97$^a$ | 111.92 ± 5.83$^a$ | −11.86$^†$ | −20.80$^†$ | −26.24$^†$ |

$^a$p < 0.05; $^b$p < 0.01 compared with Placebo
$^†$p < 0.05; $^‡$p < 0.01 compared with Initial; intra-group analysis

TABLE 5

Plasma LDL cholesterol level: effectiveness of IGOB131

| | LDL cholesterol (mean mg/dL) | | | | Change (%) | | |
| --- | --- | --- | --- | --- | --- | --- | --- |
| | Initial | 4 weeks | 8 weeks | 10 weeks | 4 Weeks-Initial | 8 Weeks-Initial | 10 Weeks-Initial |
| Placebo | 77.42 ± 9.19 | 76.46 ± 8.93 | 74.11 ± 9.29 | 73.67 ± 8.25 | −1.24 | −4.28 | −4.84 |
| IGOB131 | 82.21 ± 8.06 | 71.81 ± 5.92[b] | 64.73 ± 8.91[b] | 59.77 ± 4.98[b] | −12.65[‡] | −21.26[‡] | −27.30[‡] |

[a]$p < 0.05$; [b]$p < 0.01$ compared with Placebo
[†]$p < 0.05$; [‡]$p < 0.01$ compared with Initial; intra-group analysis

TABLE 6

Fasting blood glucose levels: effectiveness of IGOB131

| | Blood glucose (mean mg/dL) | | | | Change (%) | | |
| --- | --- | --- | --- | --- | --- | --- | --- |
| | Initial | 4 weeks | 8 weeks | 10 weeks | 4 Weeks-Initial | 8 Weeks-Initial | 10 Weeks-Initial |
| Placebo | 81.42 ± 9.63 | 79.49 ± 10.10 | 77.81 ± 9.41 | 77.12 ± 7.80 | −2.37 | −4.43 | −5.28 |
| IGOB131 | 85.55 ± 5.59 | 76.64 ± 10.29[a] | 68.74 ± 9.25[a] | 66.30 ± 4.93[a] | −10.41[†] | −19.65[†] | −22.50[†] |

[a]$p < 0.05$; [b]$p < 0.01$ compared with Placebo
[†]$p < 0.05$; [‡]$p < 0.01$ compared with Initial; intra-group analysis

TABLE 7

C-reactive protein levels: effectiveness of IGOB131

| | (mean mg/dL) | | | | Change (%) | | |
| --- | --- | --- | --- | --- | --- | --- | --- |
| | Initial | 4 weeks | 8 weeks | 10 weeks | 4 Weeks-Initial | 8 Weeks-Initial | 10 Weeks-Initial |
| Placebo | 1.462 ± 0.045 | 1.455 ± 0.041 | 1.445 ± 0.032 | 1.445 ± 0.049 | 0.48 | 1.16 | 1.16 |
| IGOB131 | 1.490 ± 0.041 | 0.911 ± 0.049[a] | 0.712 ± 0.044[b] | 0.715 ± 0.049[b] | 38.86[†] | 52.21[‡] | 52.01[‡] |

[a]$p < 0.05$; [b]$p < 0.01$ compared with Placebo
[†]$p < 0.05$; [‡]$p < 0.01$ compared with Initial; intra-group analysis

TABLE 8

Adiponectin levels: effectiveness of IGOB131

| | Blood adiponectin (mean mg/l) | | | | Change (%) | | |
| --- | --- | --- | --- | --- | --- | --- | --- |
| | Initial | 4 weeks | 8 weeks | 10 weeks | 4 Weeks-Initial | 8 Weeks-Initial | 10 Weeks-Initial |
| Placebo | 12.11 ± 3.21 | 15.18 ± 3.50 | 14.63 ± 3.47 | 14.94 ± 3.92 | 25.35 | 20.81 | 23.37 |
| IGOB131 | 12.16 ± 3.04 | 24.84 ± 3.81[a] | 30.95 ± 3.96[b] | 31.59 ± 3.85[a] | 104.28[†] | 154.52[‡] | 159.79[†] |

[a]$p < 0.05$; [b]$p < 0.01$ compared with Placebo
[†]$p < 0.05$; [‡]$p < 0.01$ compared with Initial; intra-group analysis

TABLE 9

Leptin levels: effectiveness of IGOB131

| | Serum leptin (mean ng/ml) | | | | Change (%) | | |
| --- | --- | --- | --- | --- | --- | --- | --- |
| | Initial | 4 weeks | 8 weeks | 10 weeks | 4 Weeks-Initial | 8 Weeks-Initial | 10 Weeks-Initial |
| Placebo | 31.39 ± 1.83 | 29.39 ± 1.39 | 28.18 ± 1.84 | 28.45 ± 1.86 | 6.37 | 10.23 | 9.37 |
| IGOB131 | 32.96 ± 1.63 | 18.12 ± 1.38[a] | 16.84 ± 1.25[a] | 16.91 ± 1.36[b] | 45.02[†] | 48.91[†] | 48.70[‡] |

[a]$p < 0.05$; [b]$p < 0.01$ compared with Placebo
[†]$p < 0.05$; [‡]$p < 0.01$ compared with Initial; intra-group analysis

The invention claimed is:
1. A method of decreasing LDL and total cholesterol levels in a human, the method comprising:
   administering a composition containing about 300 mg of *Irvingia gabonensis* seed extract to a human once daily to decrease LDL cholesterol levels by at least 27% in the human and total cholesterol levels by at least 26% in the human.

* * * * *